(12) United States Patent
Kanik et al.

(10) Patent No.: US 6,794,645 B2
(45) Date of Patent: Sep. 21, 2004

(54) PROTON-TRANSFER-REACTION/ION-MOBILITY-SPECTROMETER AND METHOD OF USING THE SAME

(75) Inventors: Isik Kanik, Monrovia, CA (US);
Luther W. Beegle, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/283,488

(22) Filed: Oct. 30, 2002

(65) Prior Publication Data

US 2003/0116705 A1 Jun. 26, 2003

Related U.S. Application Data

(60) Provisional application No. 60/334,437, filed on Nov. 30, 2001.

(51) Int. Cl.[7] .............................. B01D 59/44
(52) U.S. Cl. ................ 250/288; 250/281; 250/282; 250/283; 250/286; 250/287
(58) Field of Search ................ 250/286, 287, 250/288, 281, 282, 283

(56) References Cited

U.S. PATENT DOCUMENTS

| | | | | |
|---|---|---|---|---|
| 4,551,624 A | * | 11/1985 | Spangler et al. | ............ 250/287 |
| 6,518,567 B1 | * | 2/2003 | Ganeev et al. | ............ 250/282 |
| 6,690,005 B2 | * | 2/2004 | Jenkins et al. | ............ 250/287 |
| 6,693,276 B2 | * | 2/2004 | Weiss et al. | ................ 250/288 |

* cited by examiner

Primary Examiner—John R. Lee
Assistant Examiner—Erin-Michael Gill
(74) Attorney, Agent, or Firm—Daniel L. Dawes; Myers Dawes Andras & Sherman LLP

(57) ABSTRACT

A high-pressure hollow cathode ionizer is combined with an ion-mobility-spectrometer (IMS) for the detection of trace amounts of organic compounds in gas. The ionizer uses $H_3O^+$, ions which do not react with air to ionize the organic compounds and the organic compounds are soft ionized. The ionized organic compounds are detected in the IMS at levels of parts per billion and identified using calibrated reference tables. Applications include but are not limited to the fields of: (1) medicine as a breath analyzer for detection of lung cancer, diabetes, liver cirrhosis, (2) law enforcement in drug interdiction and explosives detection, (3) food monitoring and control, (4) environmental monitoring and (5) space applications.

20 Claims, 4 Drawing Sheets

PROTON-TRANSFER-REACTION/ION-MOBILITY-SPECTROMETER AND METHOD OF USING THE SAME

RELATED APPLICATIONS

The present application is related to U.S. Provisional Patent Application serial No. 60/334,437, filed on Nov. 30, 2001, which is incorporated herein by reference and to which priority is claimed pursuant to 35 USC 119.

The present application was funded at least in part by NASA funding pursuant to Grant No. NAS7-1407 and may be subject to government rights.

BACKGROUND OF THE INVENTION

1. Field of the Invention

The invention relates to the field of ionizers combined with ion-mobility spectrometers (IMS) for the detection of trace amounts of organic compounds in gas and methods of using the same.

2. Description of the Prior Art

Miniature mass spectrometry is a powerful in-situ tool for identifying a wide variety of chemical compounds. For applications that cover many disciplines such as planetary exploration, residual gas analysis, and environmental applications, there is a need for an in-situ analytical separation device or chemical sensor which is rugged, light weight, low power, small, fast, and requires minute quantities of sample for analysis. These requirements are also applicable for the detection of certain organics in the medical sciences (analyzing human breath to detect compounds associated with certain deadly diseases such as lung cancer and cirrhosis of the liver), for a chemical sensor for use on the battlefield (chemical warfare agents), law enforcement (drug interdiction and explosives detection), and food monitoring and control.

Gas chromatography/mass spectrometry (GC/MS) is perhaps the most prominent of current techniques presently available for the analysis of organic compounds. However, conventional GC/MS detectors have three notable shortcomings. First there is limited sensitivity. Commonly used GC/MS detectors likely lack the sensitivity needed to detect organic compounds at the sub parts-per-billion (ppb) level, a necessity that should be a requirement for in-situ chemical analysis. Second, the fragmentation of large organic species prevents accurate identification of organic samples. When a mixture of organic components is to be analyzed, the complexity of breakup patterns puts very severe constraints on the quantitative analysis of the concentrations of these components. Third, strenuous vacuum requirements. In conventional GC/MS systems require a high vacuum environment which greatly increases the size, weight and mechanical complexity. A new detector that will circumvent these problems (i.e. a detector which does not need a complicated vacuum system to operate, has detection sensitivity at levels below parts per-billion and is free from any fragmentation problem) is needed.

BRIEF SUMMARY OF THE INVENTION

The invention is an apparatus which combines a novel high-pressure (~1–5 Torr) hollowcathode ionizer and an ion-mobility-spectrometer (IMS) for the detection of trace amounts of organic compounds. The detector uses a novel "soft-ionization technique", based on a proton-transfer reaction involving $H_3O^+$, to efficiently ionize (e.g. >95%) most large molecules without fragmentation. This is critical for the unambiguous identification of species. In addition, $H3O^+$ ions do not react with clean air. The result is that the normal components of air ($O_2$, $N_2$, $CO_2$, CO, and the like) pass through the detector and do not get detected with the spectra of most organic compounds. The advantages of this approach in comparison to commonly used gas chromatography/mass spectrometry (GC/MS) is extremely low background signal owing to the inherent filtering capabilities of our novel $H_3O^+$ ionization technique, increased sensitivity, no fragmentation of large organic species, and no high vacuum requirements. The unit can operate under atmospheric conditions. In addition, the cost of this unit is at the time of filing expected to be in the range of $3–6000, which is much less than typical GC/MS units. Finally, the instrumentation is relatively small. For example a laptop computer used to acquire the data is larger than the instrumentation and supporting electronics. Applications of the invention to the fields of: (1) medicine as a breath analyzer for detection of lung cancer, diabetes, liver cirrhosis, etc., (2) law enforcement in drug interdiction and explosives detection, (3) food monitoring and control, (4) environmental monitoring and (5) space applications such as searching chemical signatures of life on outer planets are expected to be substantial and only a very partial list were utility can be found.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
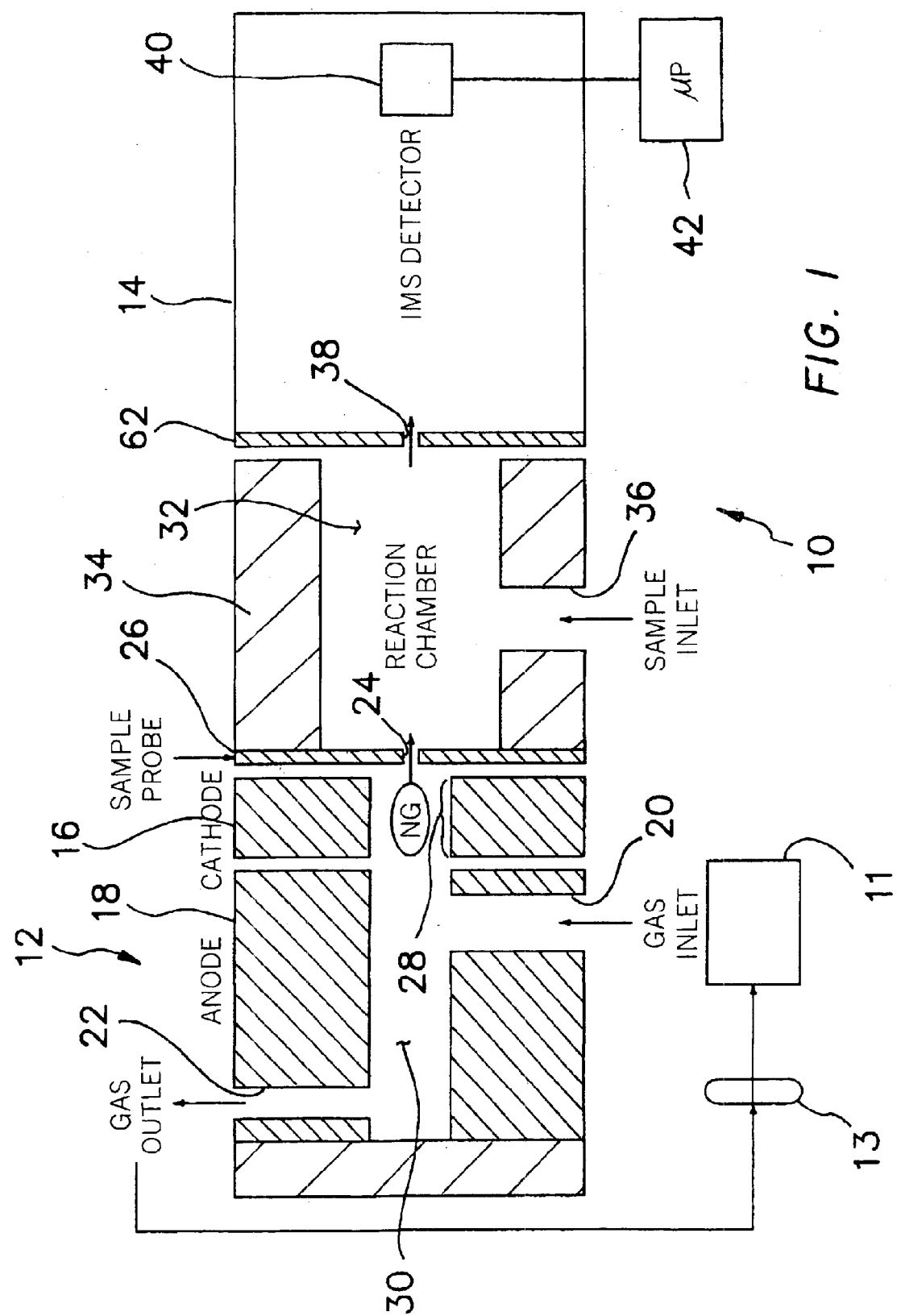
FIG. 1 is a block diagram of the combination of the ionizer, reaction chamber and IMS detector of the invention.

The invention is a small, portable detector system, generally denoted by reference numeral 10 in FIG. 1, with high sensitivity in the range of subparts-per-billion and suitable for detection of a trace amount of organic compounds in a gas or air. The system design does not suffer from the problems normally associated with commonly used gas chromatography/mass spectrometry (GC/MS) based instruments such as limited sensitivity, fragmentation of large organic species and high vacuum requirements. System 10, which is light weight and consumes approximately 10 W power or less, is adapted, for example, for in-situ investigations on planetary bodies. There is also a great potential to utilize system 10 with minor or no modification in medicine as breath analyzer for early detection of certain deadly diseases. Military and law enforcement applications also exist. Finally, use as an air quality detector aboard the space station is planned. Many more applications of system 10 exist or can be devised and these categories do not exhaust the range of possibilities.

One of the problems to which system 10 is directed to is to provide a high sensitivity (ppb) detection technique for searching chemical signatures of life on planetary bodies, particularly on Mars. Therefore there was a need to develop and demonstrate a novel detection technique, which has distinct advantages over the commonly used GC/MS based instruments. System 10 possesses high sensitivity, does not suffer from a fragmentation problem of large organic species and significantly to planetary applications, it does not need high vacuum which greatly increases size, weight and mechanical complexity.

What has been provided to meet this need is a system 10 which combines a novel high-pressure (1–5 Torr) hollow cathode ionizer 12 and a conventional ion-mobility-spectrometer (IMS) 14. Although the specific IMS 14 used can be chosen according to the application requirements at hand, in the illustrated embodiment an IMS 14, made by the Jet Propulsion Laboratory located at Pasadena, Calif., is used. The details of IMS 14 are not critical to the invention and therefore will not be further described except to the extent necessary to provide an explanation of the relationship of the components.

Figure 2:
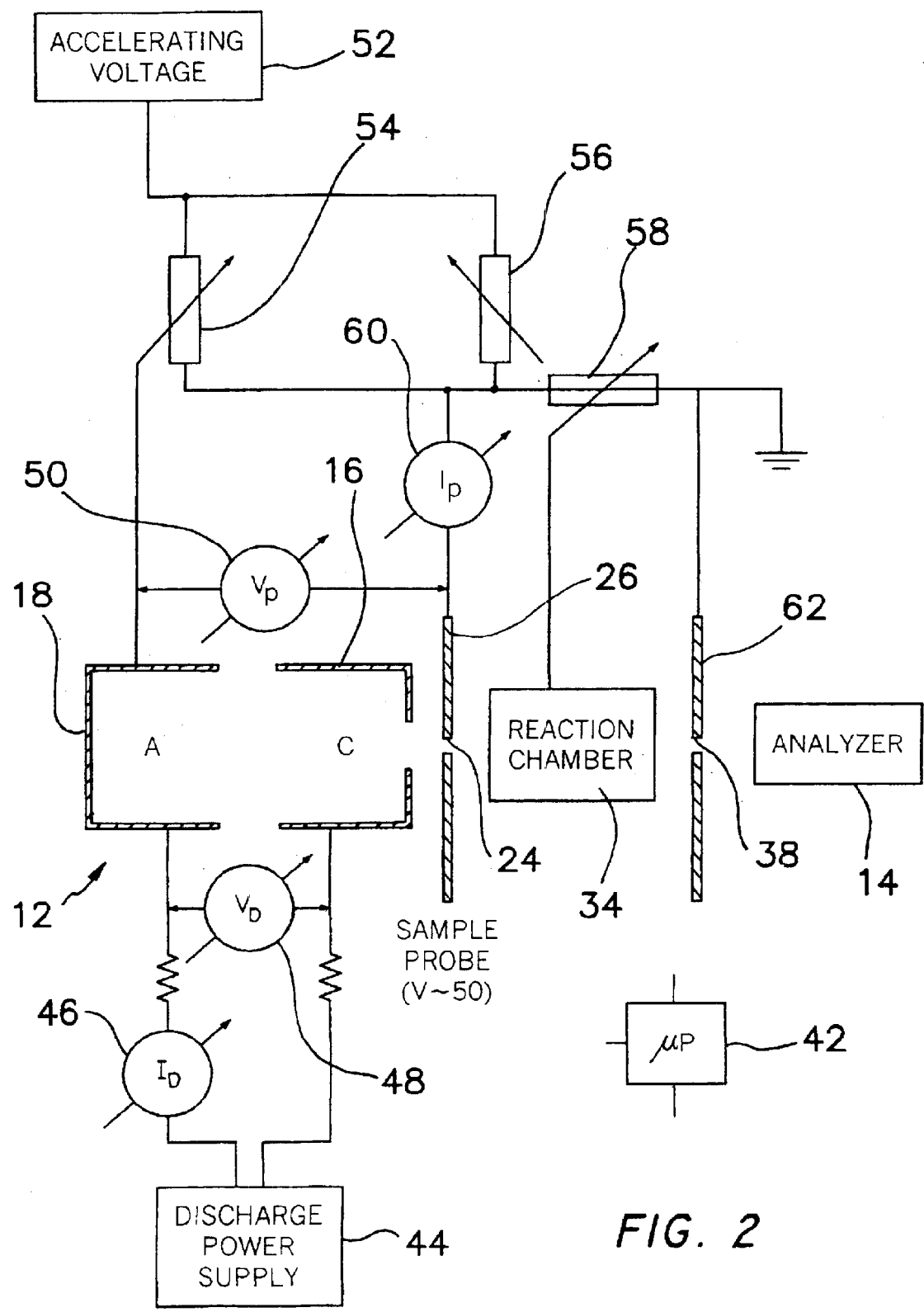
FIG. 2 is a block diagram of the control and power circuitry associated with the combination of FIG. 1.
Figure 3A:
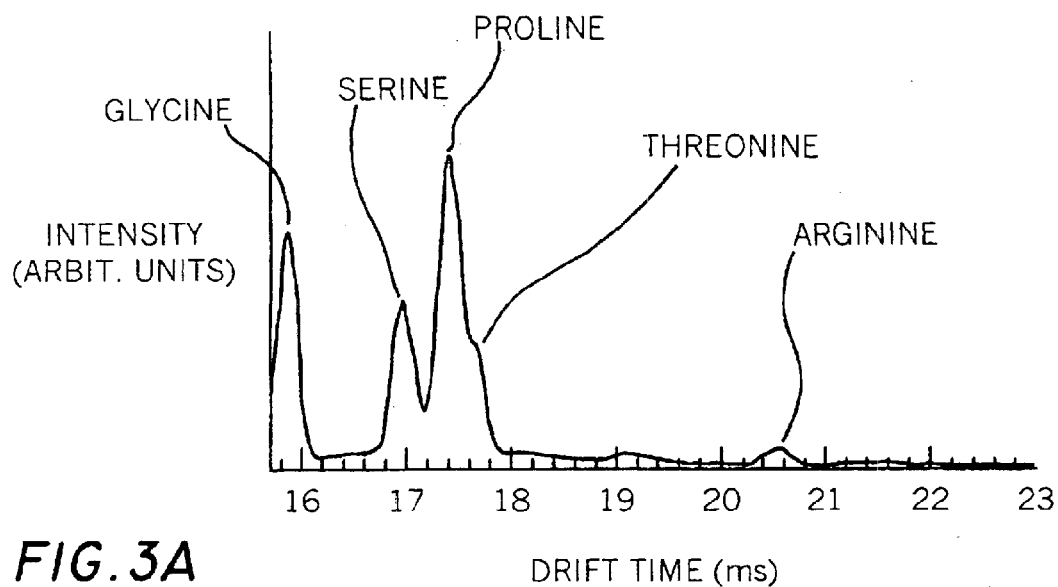
FIGS. 3a–3d are graphs of the data output from the instrument of FIGS. 1 and 2.
Figure 3B:
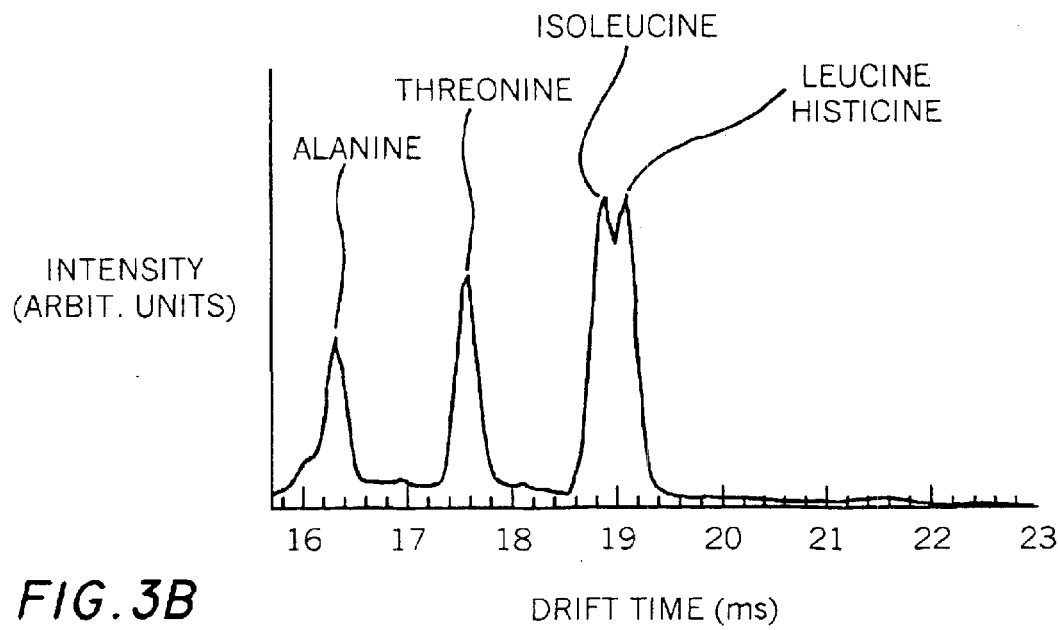
Figure 3C:
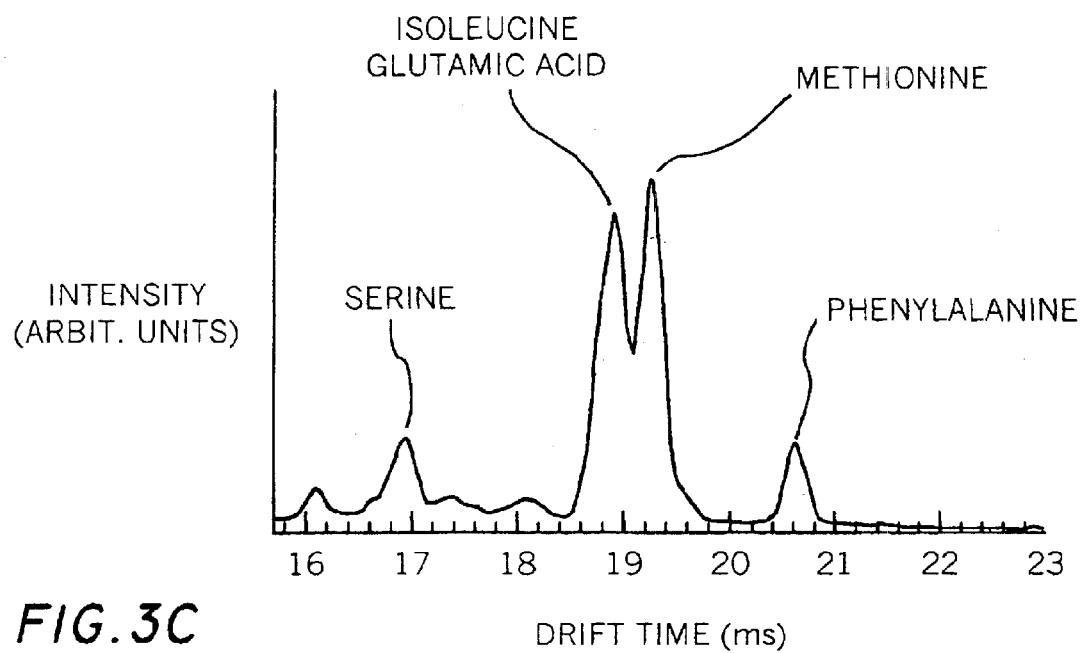
Figure 3D:
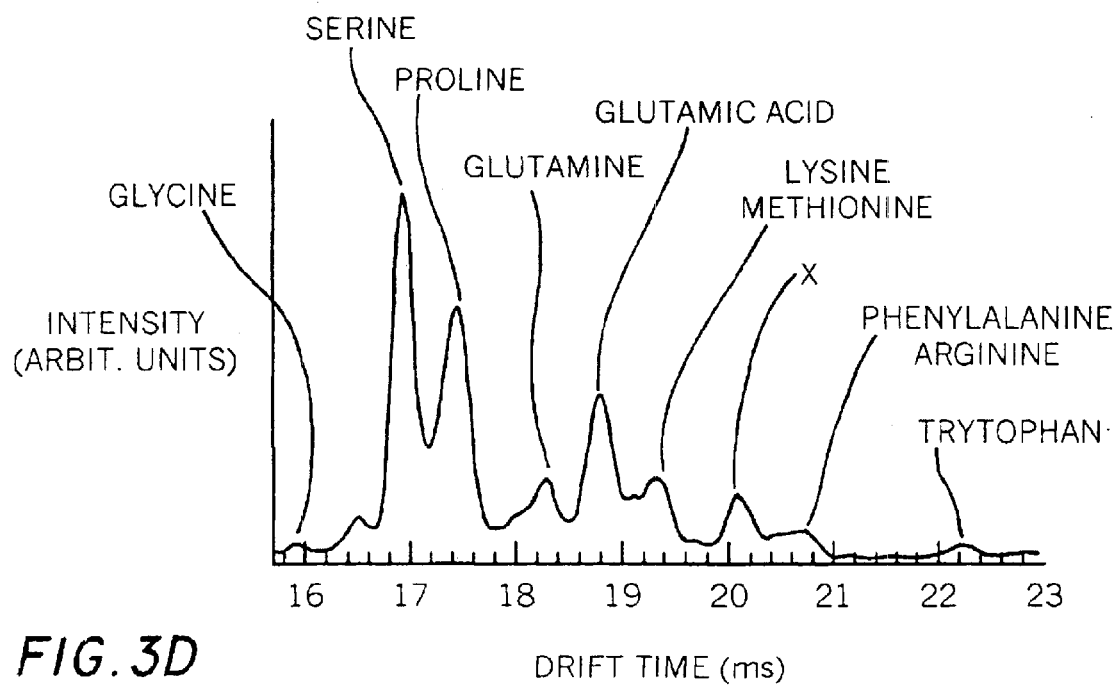

Ionizer 12 operates on the fundamental properties of the proton-transfer-reaction (PTR):

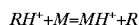

where $RH^+$ is the reactant ion, $H^+$ is a proton, R is the reactant gas, $MH^+$ is a product ion and M is a molecule. The reactant molecule, R, can be chosen so that its proton affinity is slightly less than the proton affinity of the target molecule, M, in which case the probability for fragmentation channels of the reaction is low and the process of what is defined here as "soft" ionization is dominant. The process is called a soft ionization because the energy of the reaction does not fragment the molecule like in traditional electron-impact ionization. In addition, the molecule of interest is singly ionized and multiple ionization is substantially avoided. Thus, according to the invention, the voltages and currents employed in ionizer 12 as diagrammatically depicted in FIG. 2 are modified to realize the soft or single ionization of only the class of molecules of interest, while leaving other molecules know or suspected to be present, which are not of interest, nonionized.

Moreover, the reaction is highly selective i.e., molecules which have a proton affinity lower than the reactant do not enter the reaction. $H_3O^+$ is the most suitable proton donor for investigating trace components in the Martian air because these ions do not react with $CO_2$, CO, $H_2O$, $O_2$, $N_2$, He, Ne, Ar, Xe etc. which are the prime constituents of present day Martian atmosphere. Many different choices of the reactant ion, $RH^+$, other than $H_3O^+$, can be made according to teachings of the invention according to the molecule M to be detected. For example, the reactant ion is chosen according to the proton affinity of the molecule to be ionized. For example, if you seek to detect $NO_2$ in a $N_2O$ environment, $SF_6H^+$ (proton affinity 575 kJ/mol) would be chosen as reactant ion, since $N_2O$'s proton affinity (549 kJ/mol) is smaller than for $NO_2$ (591 kJ/mol).

IMS detection has been chosen for detecting trace amounts of ionized organic compounds because it provides benefits, which cannot be matched readily or reliably by other techniques. Notably, it possesses high sensitivity, which is defined here as detection limits in the low parts-per-billion range, offers a vastly improved molecular range, and does not require high vacuum for operation.

The ionizer uses a high-pressure hollow cathode source (HOS) 12 to create reactant ions ($H_3O^+$) with a high purity. The hollow cathode discharge electrode system or source 12 is comprised of a coaxial cylindrical hollow cathode 16 and anode 18 axially aligned with each other, which operate typically under approximately 1–5 Torr pressure provided by a vacuum pumping subsystem 11 communicated with gas inlet 20. Water vapor is supplied in small amounts from a water source 13 such as pressure storage tanks or vessels. The reactant gas is supplied though a small hole 36 in the bottom of reaction chamber 32. For example, for use in an air monitor aboard the space station, air is introduced through a small leak (~5 micron in diameter) where it will react with the $H_3O^+$ molecule and be detected. The nonionized reactant components are supplied through inlet 20 and if not ionized circulate in a closed system, exiting from ionizer 12 through gas outlet 22. Nonionized reactant components are circulated through the detector 14 for the purpose of ion mobility spectroscopy, which requires an inert drift gas to separate ions of differing mass. A extraction lens 62 is located in front of IMS 14 so that ions can be extracted into the IMS 14. This allows for the reactant ions to be more localized in the reactant region.

Anode 18 and cathode 16 coupled to a discharge power supply 44 shown diagrammatically in FIG. 2. The current supplied to anode 18 is in the illustrated embodiment of the order of 1 mA with the voltage potential between anode 18 and cathode 16 held at about the order of 500 volts. Both discharge current and voltage are monitored by conventional ammeter 46 and voltmeter 48, respectively. The potential difference between anode 18 and sample probe 26 is monitored by ammeter 60 voltmeter 50 and is of the order of 800 Volts. An accelerating voltage of the order of 100 volts from source 52 is applied to anode 18. Ammeter 60 is used for monitoring how much ion current is generated. Variable power supplies 54, 56, and 58 are used to set the voltages to increase or decrease the ion current dependent on the application. Variable power supply 54 is coupled to anode 18, variable power supply 56 is coupled to sample probe 26 and variable power supply 58 is coupled to reaction chamber 34. Meters 46, 48, 50 and 60 are coupled to a software controlled computer 42, which acts as a control circuit to control power supplies 44, 52, 54, 56 and 58. Computer 42 could also be replaced by conventional logic and customized control circuitry if desired.

When an ionized discharge is formed in the reactant gas, a relatively dense plasma is created in ionizer 12 which is comprised mostly of energetic electrons and reactant ions. The distribution of ions is axially symmetric in the embodiment of FIG. 1 where a symmetric ionizer 12 is used. Thus, the ions are easily extracted through a hole 24 in the center of one of the enclosing plates or sample probe 26, which is positioned practically "on" the plasma potential, because the bulk of the ionizing potential is concentrated in the cathode fall region 28. Plate 26 is also called the "sample probe". The plasma potential is created by putting a potential on anode 18 and cathode 16. This voltage, which is measured by voltmeter 48 at 5 Torr is on the order of 500 Volts. It turns out that this voltage is independent of the voltage generated by the discharge power supply 44. The extracted ions drift through the ion source drift chamber 30 in ionizer 12. This type of ion source is much more efficient in generating pure reactant ions than electron impact ionization sources. However, it is entirely within the scope of the invention to employ other types of ion sources now known or later devised for other embodiments of ionizer 12.

The gas sample to be analyzed is introduced into the reaction region 32 of reaction chamber 34 where organic molecules undergo proton-transfer reactions and form positive ions or product ions with a high efficiency according to the reaction equation above. The proton transfer reaction occurs between the ions in region 32, which are drifting in the electric field along the axis of the chamber 34 or what is defined here as the drift region 32, which is electric field created by means of two electrodes (not shown) maintained by power supply 58 at different potentials, and target molecules present in the gas sample introduced through sample inlet 36.

The second component of system 10 is provided by means of ion mobility spectrometry (IMS) 14. IMS 14 provides detection and mass-analysis of the product ions $MH^+$ for organic compounds. The IMS detection technique has been chosen for detecting trace amounts of organic compounds, because it provides benefits, which cannot be matched readily or reliably by other techniques. Of particular importance, the IMS technique offers detection limits in the parts-per-billion range. In addition, it offers a vastly improved molecular range, and does not require a high vacuum for operation. The reactant ions $RH^+$ and product ions $MH^+$ with specific polarity are caused to drift in the axial direction within system 10 by imposing an electric field by means of a bias voltage. Either positive or negative ions can be detected, depending on the polarity of the bias voltage.

In order to determine the drift velocity, the reactant ions $RH^+$ are introduced into the drift region 32 of reaction chamber 34 in a pulsatile manner, i.e. time-dependent manner by means of providing a pulsed potential on sample probe or plate 62. Within the drift region of the IMS detector 32, the product ions $MH^+$ will undergo spatial separation based on size, mass, and shape. For a given electric field E, in drift region 32 the electric field in the entire drift region is constant in both time and position. The ion drift velocity is directly proportional to the specific mobility of the product ions $MH^+$. Smaller ions travel faster, and thus have higher mobility than the larger ions that arrive later at input orifice 38 to IMS detector 14. By measuring the ion drift times for a particular set of conditions, one is then able to construct ion mobility reference tables that are used for identification of target ion species. In operation, the product ions $MH^+$ are introduced into the mass analyzer 14 via a series of pulses (repeated every 20 to 40 ms). A high-gain electrometer 40 in IMS 14 detects the resulting signal, which is typically at the pico-ampere ($10^{-12}$ A) level. A microprocessor 42 coupled to electrometer 40 handles data acquisition, processing, communication and display, as well as control and monitoring of temperature and timing. Microprocessor 42 monitors temperature and pressure because in ion mobility spectroscopy the ion mobilities ($K_o$) must be normalized to those at atmospheric pressure and temperatures ($K_m$) to be able to identify the ions. That is:

$$K_o = (T/273)(760/P)K_m$$

Where T is the Temperature in Kelvin, P is the Pressure in Torr. In the operation of instrument 10 $K_m$ is measured, and related back to $K_o$ which is a fundamental number dependent on the ion. FIGS. 3a–3d are graphs of composite spectra of four different prepared test mixtures. Peaks for each are marked with the corresponding constituent of the prepared test mixture, as determined from the calculated $K_o$ values of each peak with a comparison to that of known values of the corresponding constituent.

Because the detector uses the most suitable proton donor, which in the illustrated embodiment is $H_3O^+$ in the sense that there is no reaction with the components of air or those portions of the sample for which no reactions are sought, and is capable of identifying volatiles or organic molecules at the ppb level, several applications have been identified including but not limited to medical uses (as a breath analyzer for detection of lung cancer, diabetes, and liver cirrhosis, etc., law enforcement uses for drug interdiction and explosives detection, military uses such as chemical warfare agent detection, treaty verification, food monitoring and control and environmental monitoring uses, such as NASA space station air monitoring against hydrazine, waste incineration, site remediation, fugitive emissions control.

Some of these applications will now be described in greater detail. Potential markers for particular diseases (such as lung cancer, diabetes, liver cirrhosis, etc,) are usually present in very low concentrations in the breath of patients who are suffering from these diseases. In the onset of the diseases, these biomarkers are in extremely low concentrations, nearly at the limit of existing instrumentation. Research on new on-line highly sensitive analytical methods is necessary to diagnose these deadly diseases when they are still in their early, near-onset stages.

Breath analysis has attracted scientific attention for more than 200 years: The breath of a guinea pig was analyzed and respiration and combustion processes were demonstrated to be analogous by Lavoisier and Laplace in 1784. More recently sensitive analyses have demonstrated several volatile organic compounds (VOC's) in normal human breath, many of which have been identified by gas chromatography (GC) combined with mass spectrometry (MS).

Chemical analysis for VOC's in the breath yields information about the pool of molecular compounds in the blood that diffuse across the pulmonary alveolar membrane. These compounds originate from two major sources: endogenous (i.e. products of metabolism) or exogenous (i.e. derived from outside of the body). Consequently, breath analysis potentially presents a unique window on human metabolism, and simultaneously detects exposure to volatile organic toxins in the environment, without incurring the discomfort or inconvenience of collection of body fluid. The concentration of VOC's in the alveolar airway suggests what the status of the patient's condition might be. Clinical diagnostics of breath was first reviewed by Manolis in 1983. He compiled a long list of diseases and ingestions associated with unusual odors. For example, breath acetone has been used successfully to monitor diabetics and patients on diets. Volatile sulfur organic compounds are increased in the breath of patients with periodontal disease. Other studies have also shown that certain diseases such as lung cancer, liver cirrhosis, diabetes etc., result in VOC's in much higher concentrations in unhealthy persons' breath than that of healthy ones. For example, higher concentrations of acetone, methylethylketone, n-propanol, tolualdehyde and oxepanone were found in the breath of patients who have lung cancer. Acetone concentration is greatly enhanced in the breath of persons suffering from diabetes. Similarly, propanol shows significantly enhanced concentrations in the breath of cirrhosis patients.

More recently present physical and chemical studies of environmental determinants, suspected to cause the incidence of lung cancer, are predominantly oriented toward the substances present in the ambient air as particulates. Particle size, phase, and composition of various procarcinogane substances have been related to the inception of particular types of lung cancer. Little information exists on volatile, gas trace constituents of the human breath. This lack of information, combined with poorly developed present-day sampling techniques, ensures that most breath tests are of minor clinical value. However, it is the obvious fact, sensed by olfactory receptors, that odorous, volatile substances are present in the ambient air and in the exhaled human breath (in trace quantities) as well.

The possibility that the expired air of patients with lung cancer might contain unique VOC's that could be used as markers for screening, was first investigated by Gordon et al. in 1985. In their study of 12 samples from lung cancer patients and 17 control samples, they combined gas chromatograph with multivariate statistical analysis to extract VOC's. Samples of expired breath were collected by the gas chromatograpy/mass spectrometry (GC/MS) methods and analyzed by using general computerized statistical procedures to distinguish lung cancer patients from controls. Gordon found 49 chemical compounds that had sufficient diagnostic power in the GC/MS profiles to allow complete differentiation between the two groups. Among these compounds acetone, methylethylketone and n-propanol were identified with a classification accuracy of 93%. In a more recent study conducted by O'Neil et al. in 1988, a group of patients, diagnosed with the early stages of lung cancer, are found to have 9 compounds which were identified as potential biomarkers. Table 1 gives the listing of compounds in expired-air samples from lung cancer patients with >90% occurrence. More recently, Phillips and Qreenberg in 1992, studied VOC's in alveolar breath using the ion trap detection techniques.

TABLE 1

Listing of Compounds in Expired-Air samples from lung cancer patients (Occurrence >90%)

| Chemical Compound | } | Formula | |
|---|---|---|---|
| Propenal | | $C_3H_4O$ | |
| Acetone | | $C_3H_6O$ | |
| 2-Butanone | | $C_4H_8O$ | Phenol |
| $C_6H_6O$ Benzaldehyde | | $C_7H_6O$ | Acetophenone |
| $C_8H_8O$ Nonanal | | $C_9H_{18}O$ | |
| Ethylpropanoate | | $C_5H_8O_2$ | Methylisobutenoate |
| $C_5H_8O_2$ | | | |

Although these potential markers for particular diseases such as lung cancer are in much higher concentration in the breath of patients than that of healthy subjects, they are still at a concentration level of ppb or lower. This concentration level (ppb) is below or near the limits of sensitivity of existing instrumentation. The most abundant compounds in the normal human breath isoprene and acetone are present in only nanomolar quantities whereas several other compounds are present in picomolar concentrations or lower. Research and development of a new on-line highly sensitive analytical methods are necessary for a reliable clinical diagnosis for the early stage of this disease. The apparatus and methodology of the invention provides the tool for such research.

Much development has been conducted toward using IMS for the detection of drug vapors, including illicit drugs such as cocaine, marijuana and heroin. The proposed detector has a potential for evolving into a hand-held illicit drug detector as well as an explosives detector (nitro compounds etc.) which could be utilized in airport security systems for concealed explosives.

Similarly, a rugged detector with very high sensitivity based upon the technique proposed here, and incorporated in a remote-control rover, could be used in the battlefield for detecting chemical and biological warfare agents. Hand-held models could be used for treaty monitoring purposes.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus comprising:
   an ionizing chamber to generate a plasma of reactant ions outside of the presence of the molecules of interest;
   a reaction chamber communicated with the ionizing chamber into which reaction chamber the reactant ions are disposed and in which reaction chamber the reactant ions selectively chemically react with molecules of interest having a higher proton affinity than the reactant ions to produce substantially only singly ionized product ions without appreciable fragmentation of the molecules of interest; and an ion mobility spectrometer communicated with the reaction chamber to detect the product ions.

2. The apparatus of claim 1 where the ionizing chamber comprises a cathode and anode between which a potential difference is applied for the purpose of creating a plasma of reactant ions in the ionizer for injection into the reaction chamber.

3. The apparatus of claim 2 where the cathode of the ionizing chamber is hollow and symmetric about a common longitudinal axis defined through the cathode.

4. The apparatus of claim 3 where the cathode and anode are cylindrical and commonly aligned along the common longitudinal axis.

5. The apparatus of claim 3 where the hollow cathode of the ionizing chamber and reaction chamber are aligned along the common longitudinal axis to define an axial ion drift region through the hollow cathode and anode, and reaction chamber.

6. The apparatus of claim 1 further comprising a sample probe disposed between the ionizing chamber and reaction chamber to provide pulsatile injection of reactant ions into the reaction chamber from the ionizing chamber.

7. The apparatus of claim 6 where the ionizing chamber and reaction chamber are aligned along the common longitudinal axis to define an axial ion drift region through the hollow cathode and anode, and reaction chamber so that a pusatile grouping of product ions are generated in ion drift region in the reaction chamber.

8. The apparatus of claim 7 wherein each grouping of product ions are longitudinally spread in the drift region according to mobility and delivered in such spread groupings to the ion mobility spectrometer.

9. The apparatus of claim 6 further comprising a deceleration lens disposed between the reaction chamber and the ion mobility spectrometer to control velocity of product ions form the reaction chamber to the ion mobility spectrometer.

10. The apparatus of claim 1 where the reactant ions are selected according to a proton affinity to selectively soft ionize the molecules of interest without fragmentation of the molecule of interest.

11. A method comprising:

generating a plasma of reactant ions in an ionizing chamber;

injecting the plasma of reactant ions into a reaction chamber;

injecting molecules of interest into the reaction chamber;

chemically reacting the reactant ions with molecules of interest to produce product ions in the reaction chamber; and detecting product ions in an ion mobility spectrometer communicated with the reaction chamber.

12. The method of claim 11 where generating a plasma of reactant ions in an ionizing chamber comprises generating the plasma in a hollow cathode defining an ion drift region therein when a potential difference is applied between the anode and cathode.

13. The method of claim 12 where generating the plasma in a hollow cathode comprises generating the plasma in a hollow cathode which are symmetric about a common longitudinal axis defined through the hollow cathode and hollow anode.

14. The method of claim 13 where generating the plasma in a symmetric hollow cathode comprises generating the plasma in a hollow cathode which are cylindrical and commonly aligned along the common longitudinal axis.

15. The method of claim 11 where generating the plasma in the ionizing chamber and reaction chamber comprises generating the plasma in an ionizing chamber and reaction chamber which are aligned along the common longitudinal axis to define an axial ion drift region through the hollow cathode and anode, and reaction chamber.

16. The method of claim 11 where injecting the plasma of reactant ions into a reaction chamber comprises providing pulsatile injection of reactant ions into the reaction chamber from the ionizing chamber.

17. The method of claim 16 where providing pulsatile injection of reactant ions comprises generating a pusatile grouping of product ions in ion drift region in the reaction chamber.

18. The method of claim 17 where generating a pusatile grouping of product ions comprises spreading each grouping of product ions longitudinally in the drift region according to mobility and delivering the spread groupings to the ion mobility spectrometer.

19. The method of claim 16 further comprising decelerating the grouped product ions to control their velocity from the reaction chamber to the ion mobility spectrometer.

20. The method of claim 11 where generating a plasma of reactant ions provides the reactant ions which are selected according to a proton affinity to selectively soft ionize the molecules of interest without substantial probability of fragmentation.

* * * * *